US008598880B2

(12) United States Patent
Dalveren et al.

(10) Patent No.: US 8,598,880 B2
(45) Date of Patent: Dec. 3, 2013

(54) METHOD AND APPARATUS FOR IMAGING A SUBJECT USING LOCAL SURFACE COILS

(75) Inventors: Taylan Dalveren, Aurora, OH (US); Victor Taracila, Orange Village, OH (US); David Berendt, Aurora, OH (US)

(73) Assignee: General Electric Company, Schenectady, NY (US)

( * ) Notice: Subject to any disclaimer, the term of this patent is extended or adjusted under 35 U.S.C. 154(b) by 274 days.

(21) Appl. No.: 13/110,611

(22) Filed: May 18, 2011

(65) Prior Publication Data

US 2012/0293174 A1 Nov. 22, 2012

(51) Int. Cl.
*G01V 3/00* (2006.01)
(52) U.S. Cl.
USPC .......................................... 324/318; 324/309
(58) Field of Classification Search
USPC ............................ 324/300–322; 600/407–445
See application file for complete search history.

(56) References Cited

U.S. PATENT DOCUMENTS

| | | | |
|---|---|---|---|
| 6,577,888 B1 * | 6/2003 | Chan et al. | 600/422 |
| 6,836,117 B2 | 12/2004 | Tamura et al. | |
| 7,031,763 B1 | 4/2006 | Zhang | |
| 7,049,819 B2 * | 5/2006 | Chan et al. | 324/319 |
| 7,725,159 B2 * | 5/2010 | Guan et al. | 600/422 |

* cited by examiner

*Primary Examiner* — Brij Shrivastav
(74) *Attorney, Agent, or Firm* — The Small Patent Law Group; Dean D. Small (57) ABSTRACT

A Radio Frequency (RF) coil apparatus for generating a Magnetic Resonance (MR) image includes a body adapted to be worn by a subject being scanned, the body comprising an anterior portion, a posterior portion, and a transition portion coupled between the anterior and posterior portions, a first RF receive-only saddle coil including a first coil positioned in the anterior portion and a second coil positioned in the anterior portion, the first RF saddle coil configured to be positioned on the anterior and posterior sides of the subject. An MRI imaging system and method are also described herein.

20 Claims, 9 Drawing Sheets

METHOD AND APPARATUS FOR IMAGING A SUBJECT USING LOCAL SURFACE COILS

BACKGROUND OF THE INVENTION

The subject matter disclosed herein relates generally to magnetic resonance imaging (MRI) systems, and more particularly to a method and apparatus for imaging a subject using local surface coils.

MRI or Nuclear Magnetic Resonance (NMR) imaging generally provides for the spatial discrimination of resonant interactions between Radio Frequency (RF) waves and nuclei in a magnetic field. Specifically, MRI utilizes hydrogen nuclear spins of the water molecules in the human body, which are polarized by a strong, uniform, static magnetic field of a magnet. This magnetic field is commonly referred to as $B_0$ or the main magnetic field. When a substance, such as human tissue, is subjected to the main magnetic field, the individual magnetic moments of the spins in the tissue attempt to align with the main magnetic field. When excited by an RF wave, the spins precess about the main magnetic field at a characteristic Larmor frequency. A signal, emitted by the excited spins, is received by a conventional RF coil. The output from the RF coil is then utilized to form an image.

To improve the quality of the image, specialized local coils may be utilized, such as to image a certain region or body part. For example, when performing a scan of the lower pelvic region, an endorectal coil or a torso coil maybe utilized. However, conventional endorectal coils provide a limited field of view that may not adequately cover the lower pelvic region. Moreover, conventional endorectal coils are invasive. Accordingly, when the conventional endorectal coil is inserted into the rectum to image, for example, the prostate, this coil may physically move or distort the anatomy to such an extent that the prostate is not in same position during surgery as it is during the MR scan. Additionally, because the conventional torso coil is configured to be placed on the anterior and posterior side of the patient, the Signal-to-Noise Ratio (SNR) is reduced, resulting in a lower quality image.

BRIEF DESCRIPTION OF THE INVENTION

In accordance with an embodiment, Radio Frequency (RF) coil apparatus for generating a Magnetic Resonance (MR) image is provided. The coil apparatus includes a body adapted to be worn by a subject being scanned, the body comprising an anterior portion, a posterior portion, and a transition portion coupled between the anterior and posterior portions, a first RF receive-only saddle coil including a first coil positioned in the anterior portion and a second coil positioned in the anterior portion, the first RF saddle coil configured to be positioned on the anterior and posterior sides of the subject, and a second RF receive-only saddle coil including a third coil configured to receive a subject's first leg therein and a fourth coil configured to receive a subject's second leg therein, a portion of the third and fourth coils being positioned in both the anterior portion and the posterior portion.

In accordance with another embodiment, a Magnetic Resonance Imaging (MRI) system is provided. The MRI system includes a main magnet configured to generate a main magnetic field within a bore of the imaging system, and a Radio Frequency (RF) coil apparatus configured to be worn by a subject being inserted into the bore of the imaging system. The coil apparatus includes a body adapted to be worn by a subject being scanned, the body comprising an anterior portion, a posterior portion, and a transition portion coupled between the anterior and posterior portions, a first RF receive-only saddle coil including a first coil positioned in the anterior portion and a second coil positioned in the anterior portion, the first RF saddle coil configured to be positioned on the anterior and posterior sides of the subject, and a second RF receive-only saddle coil including a third coil configured to receive a subject's first leg therein and a fourth coil configured to receive a subject's second leg therein, a portion of the third and fourth coils being positioned in both the anterior portion and the posterior portion.

In accordance with a further embodiment, a method of imaging a subject using a Magnetic Resonance Imaging (MRI) system is provided. The method includes positioning a subject within an RF coil apparatus such that a first RF receive-only coil is positioned in the anterior portion of the subject, a second RF receive-only coil is positioned on an anterior portion of the subject, a third RF coil is positioned around a first leg of the subject, and a fourth RF receive-only coil is positioned around a second leg of the subject, and generating an image of the subject using information received from the first, second, third and fourth RF receive-only coils.

DETAILED DESCRIPTION OF THE INVENTION

Embodiments described herein will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide an apparatus and method for imaging a lower pelvic region using two pairs of localized radio frequency (RF) receive coils arranged for quadrature detection. In various embodiments, the pair of RF receive coils are positioned proximate to the subject's prostate gland to improve imaging of the prostate gland.

Figure 1:
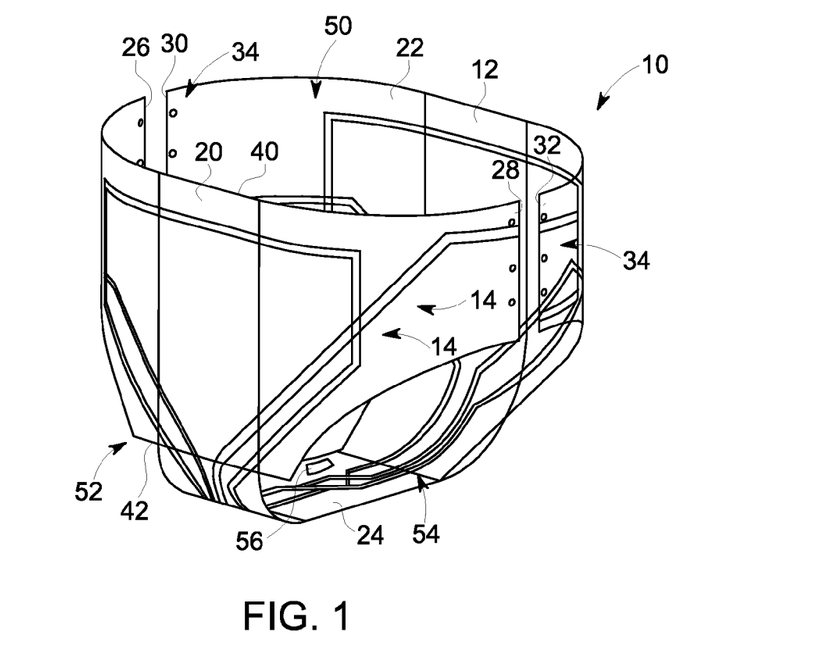
FIG. 1 is a perspective view of a Magnetic Resonance Imaging (MRI) coil apparatus formed in accordance with various embodiments.
Figure 2:
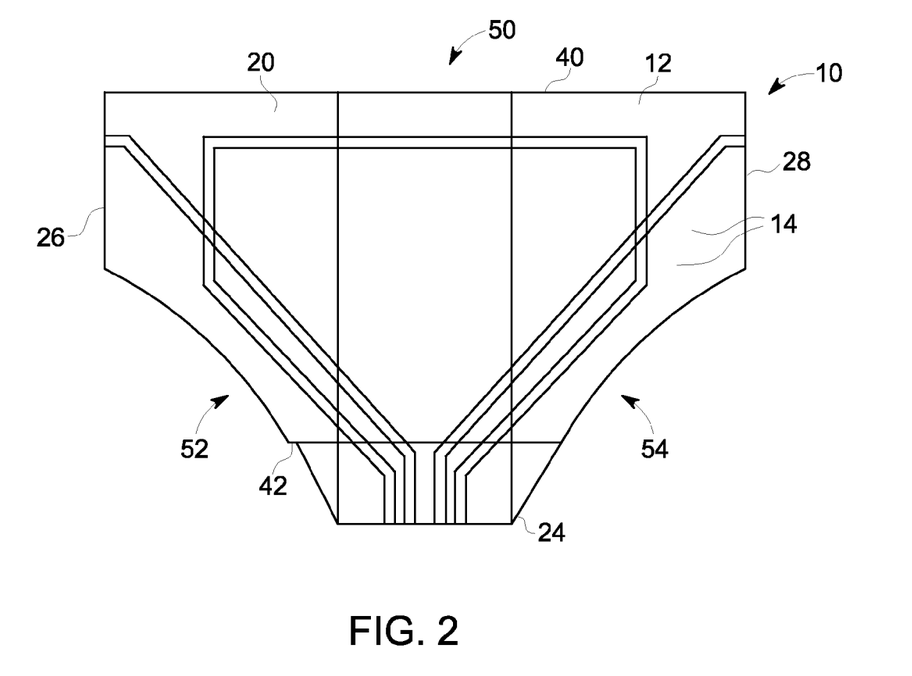
FIG. 2 is a front view of the coil apparatus shown in FIG. 1.
Figure 3:
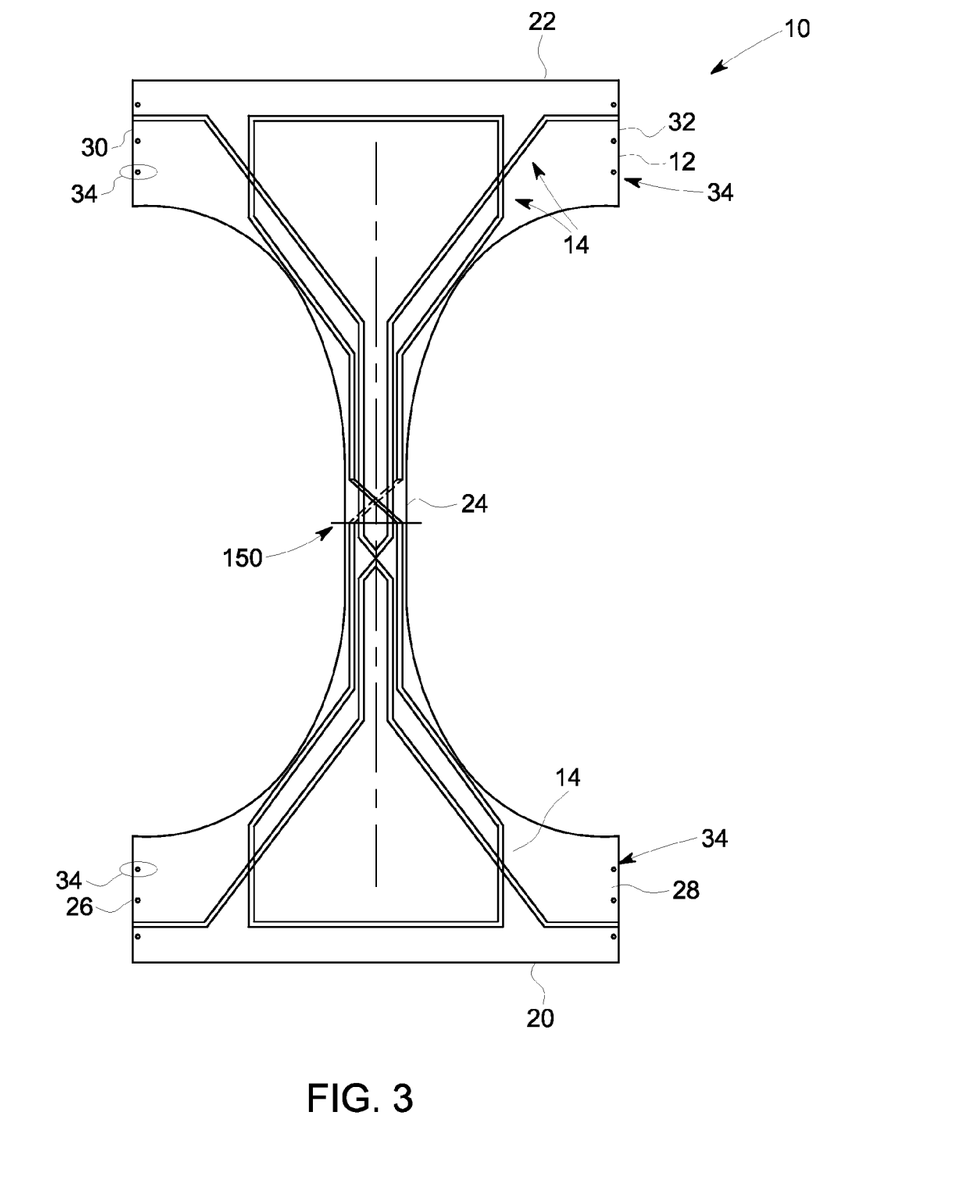
FIG. 3 is a top planar view of the coil apparatus shown in FIG. 1.

FIG. 1 is a perspective view of an MRI coil apparatus 10 formed in accordance with various embodiments. FIG. 2 is a front view of the coil apparatus 10 shown in FIG. 1. FIG. 3 is a planar view of the coil apparatus 10 shown in FIGS. 1 and 2. The coil apparatus 10 includes a flexible body 12 that has a plurality of receive-only RF coils 14. The RF coils 14 may be attached to an internal surface of the flexible body 12, to an external surface or the flexible body 12, embedded within the flexible body 12, or a combination thereof. The RF receive coils 14 are discussed in more detail below. In the exemplary embodiment, the coil apparatus 10 is a portable coil apparatus that is configured to be worn by a subject (not shown) during an MRI scan. Accordingly, the flexible body 12 includes an anterior portion 20, a posterior portion 22, and a transition portion 24 that couples the anterior portion 20 to the posterior portion 22. In the exemplary embodiment, the flexible body 12 is formed as a single unitary structure that includes the anterior portion 20, the posterior portion 22, and the transition portion 24. Optionally, the anterior portion 20, the posterior portion 22, and the transition portion 24 may be formed as separate structures that are physically connected together to form the flexible unitary body 12.

The anterior portion 20 includes a first end 26 and a second end 28. The posterior portion 22 also includes a first end 30 and a second end 32. The first ends 26 and 30 are configured to be removably coupled together. Additionally, the second ends 28 and 32 are configured to be removably coupled together. The first ends 26 and 30 may be coupled to the second ends 28 and 32, respectively, using a fastener device 34. The fastener device 34 may be embodied as any suitable fastening mechanism, such as mechanical hooks, a button, a hook and loop fastener, etc.

In use, the coil apparatus 10 is configured to be worn by the subject. Accordingly, the anterior portion 20 has a substantially triangular shape to enable the anterior portion 20 to be positioned on the anterior side of the subject. Moreover, the posterior portion 22 also has a substantially triangular shape to enable the posterior portion 22 to be positioned on a posterior side of the subject. As shown in FIGS. 1 and 2, the anterior and posterior portions 20 and 22 taper inwardly from a first end 40, that is positioned near the naval of the subject when worn, to a second end 42 that is physically connected to the transition portion 24. Accordingly, when the first ends 26 and 30 are physically connected together and the second ends 28 and 32 are physically connected together, the flexible body 12 defines a first opening 50 extending therethrough. The first opening 50 is sized to receive the subject's torso therethrough. The flexible body 12 also has a second opening 52 and a third opening 54. The second opening 52 is sized to receive the subject's right leg therethrough. Similarly, the third opening 54 is sized to receive the subject's left leg therethrough. In various embodiments, the flexible body 12 may also include an additional opening 56 extending therethrough. The opening 56 may be configured to receive a medical instrument therethrough. More specifically, the opening 56 may be utilized by an operator to insert a medical surgical and/or imaging device therethrough to enable an operator to view an image of the subject generated using the coil apparatus 10 and concurrently utilize a medical device while viewing the image.

The flexible body 12 is preferably fabricated from a flexible foam material to enable the flexible body 12 to expand and/or contract to fit a variety of subjects having physical anatomies of different sizes. Optionally, the flexible body 12 may be fabricated from a cloth material, or any other suitable material that enables the flexible body 12 to conform to the torso of the subject being imaged. Thus, the size and shapes of the anterior portion 20, the posterior portion 22, and the transition portion 24 may be sized to fit subjects having different sized anatomies. For example, the size of the anterior and posterior portions 20 and 22 and/or the length of the transition portion 24 may be increased to accommodate subjects having larger anatomies. Moreover, the size of the anterior and posterior portions 20 and 22 and/or the length of the transition portion 24 may be decreased to accommodate subjects having smaller anatomies. Therefore, the overall size of the flexible body 12 and the RF coils 14 may be fabricated in a small size, a medium size, a large size, an extra large size, etc. to fit a large variety of patients.

Figure 4:
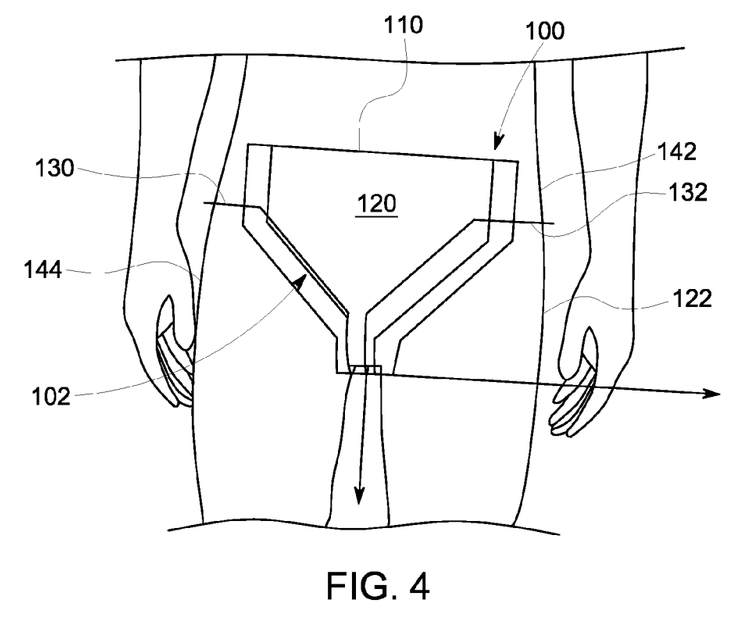
FIG. 4 is a front view of one configuration of Radio Frequency (RF) coils shown in FIGS. 1-3 formed in accordance with various embodiments.
Figure 5:
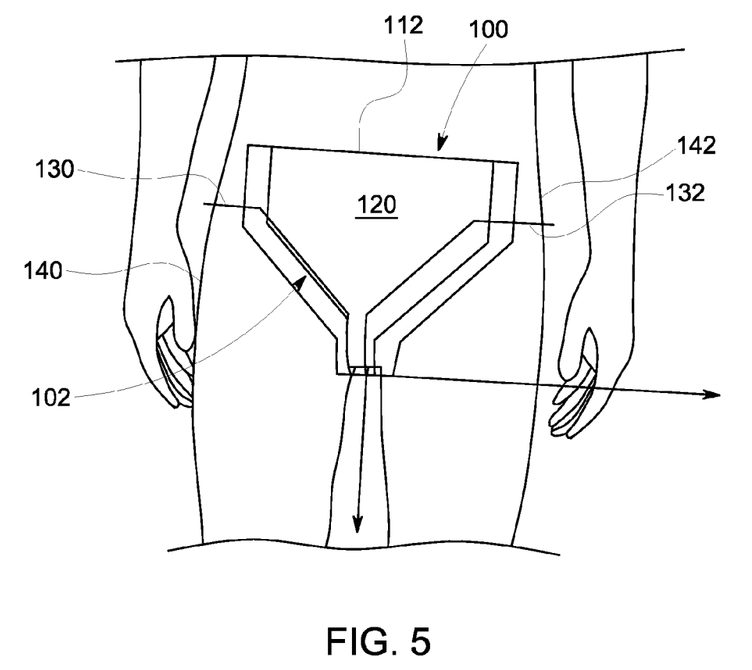
FIG. 5 is a rear view the RF coils shown in FIG. 4.

FIG. 4 is a front view of the RF coils 14 shown in FIGS. 1-3. FIG. 5 is a rear view of the RF coils 14 shown in FIG. 4. As discussed above, the coil apparatus 10 includes a plurality of receive-only RF coils 14 embedded therein. Optionally, the receive-only RF coils 14 may be attached to an internal or external surface of the flexible body 12. In the exemplary embodiment, the RF receive coils 14 include a first saddle coil 100 and a second saddle coil 102. The first saddle coil 100 has a first coil portion 110 that is configured to be positioned proximate to an anterior side 120 of the pelvis 122 and a second coil portion 112 that is configured to be positioned proximate to a posterior side 124 of the pelvis 122 to enable the pelvis 122 to be positioned between the first and second coil portions 110 and 112, respectively.

The second saddle coil 102 has a third coil portion 130 that is configured to be positioned proximate to a left side 140 of the pelvis 122 and a fourth coil portion 132 that is configured to be positioned proximate to a right side 142 of the pelvis 122 to enable the pelvis 122 to be positioned between the third and fourth coil portions 130 and 132 respectively. In the exemplary embodiment, the first and second saddle coils 100 and 102 are quadrature-arranged such that the phases of the magnetic resonance signals received from the coil portions 110, 112, 130, and 132 differ by 90 degrees, thus achieving imaging of the pelvis area 122, while concurrently achieving a relatively high SNR.

Figure 6:
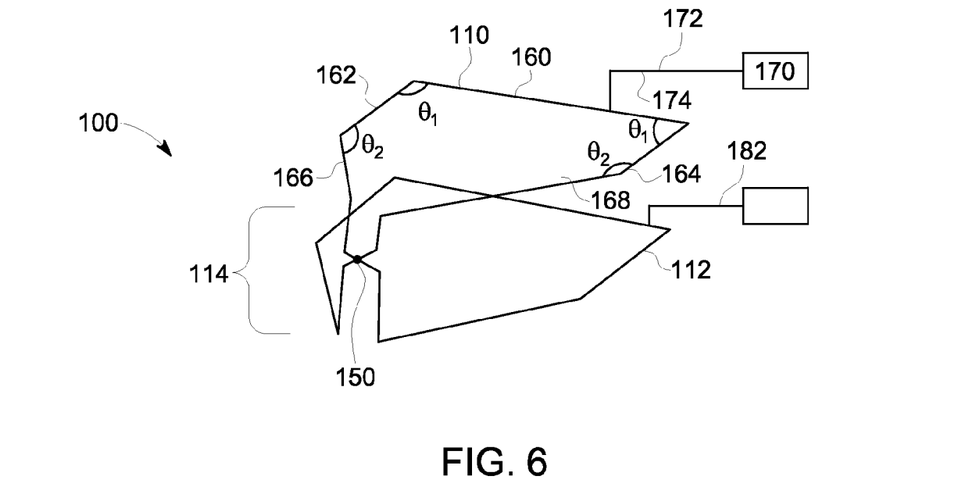
FIG. 6 is a perspective view of a first saddle coil shown in FIGS. 1-3 and formed in accordance with various embodiments.

FIG. 6 is a perspective view of the first saddle coil 100 that is configured to be positioned on the anterior side 120 and the posterior side 124 of the pelvis 122. As shown in FIG. 6, the first coil portion 110 is electrically connected to the second coil portion 112 via a coil connecting portion 114. Thus, the first coil portion 110, the second coil portion 112 and the connecting portion 114 together form the closed-loop first saddle coil 100. The coil connecting portion 114 represents two electric paths crossing proximate to a location 150. The location 150 is selected to provide optimal SNR for imaging a selected region of interest. In the exemplary embodiment, the location 150 (also shown in FIG. 3) is selected to improve the imaging of a subject's prostate gland. Accordingly, in one embodiment, the location 150 where the saddle coil 100 crosses paths is positioned externally on the subject at the location 150 that is nearest the prostate gland.

As discussed above, the first saddle coil 100 is configured as a receive only coil. Accordingly, to facilitate optimizing the SNR of the first saddle coil 100, the first and second coil portions 110 and 112, respectively, are configured to substantially cover the field-of-view (FOV) extending over the pelvic region. More specifically, the first saddle coil 100 has a shape that that is substantially similar to a shape of a subject's pelvic region to enable the first saddle coil 100 to cover the pelvic region. For example, in the exemplary embodiment, the first and second coil portions 110 and 112, respectively have a substantially trapezoidal shape. Thus, the first coil portion 110 has a first side 160, a second side 162, a third side 164, a fourth side 166, and a fifth side 168. The first side 160 is electrically connected between the second and third sides 162 and 164. Moreover, the fourth and fifth sides 166 and 168 are electrically connected between the second and third sides 162 and 164, respectively, and the connecting portion 114.

To form the exemplary trapezoidal shape, the first side 160 is disposed at an angle $\theta_1$ from the second and third sides 162 and 164. In the exemplary embodiment, the angle $\theta_1$ is approximately 90 degrees. Moreover, the second and third sides 162 and 164 are offset from the fourth and fifth sides 166 and 168, respectively, by an angle of $\theta_2$. In the exemplary embodiment, $\theta_2$ is greater than 90 degrees such that the first saddle coil 100 substantially conforms to the subject's pelvis during imaging operation. Thus, the first side 160 is configured to extend substantially perpendicular to the connecting portion 114. Moreover, the second and third sides 162 and 164 are disposed approximately perpendicular to the first side 160. Additionally, the fourth and fifth sides 166 and 168 are configured to follow the contour of the subject's pelvis to enable the first saddle coil 100 to define a FOV that covers substantially all of the subject's pelvic region and more specifically, the subject's prostate gland.

As shown in FIG. 6, the coil apparatus 10 also includes an electronics assembly 170 that, in one embodiment, is electrically connected to the first coil portion 110 via a cable 172. Optionally, the electronics assembly 170 may be wirelessly connected to the coil apparatus 10. The electronics assembly 170 generally includes an RF receiver for receiving signals from the first coil portion 110. The electronics assembly 170 may also include other suitable components such as capacitors, inductors, baluns, or other components to improve the SNR of the first saddle coil 100. In the exemplary embodiment, the cable 172 is an RF cable having a predetermined length 174. For example, a balun (balance/unbalance) device may be utilized to reduce the noise and/or stray RF currents generated due to induced currents in the RF cable 172. Specifically, in operation, the balun creates a high impedance on the RF cable 172 when the overall length of the balun is equal to one quarter of the electromagnetic radiation wavelength of the signal transmitted through the RF cable 172. Accordingly, the length 174 of the RF cable 172 is determined based on the wavelength of a signal transmitted through the RF cable 172.

In the exemplary embodiment, the second coil portion 112 is formed substantially similar to the first coil portion 110. Additionally, the second coil portion 112 may be coupled to a second electronics assembly 180 via a second RF cable 182. Optionally, the first and second coil portions 110 and 112 may be coupled to a single electronics assembly, such as electronics assembly 170, for example.

Figure 7:
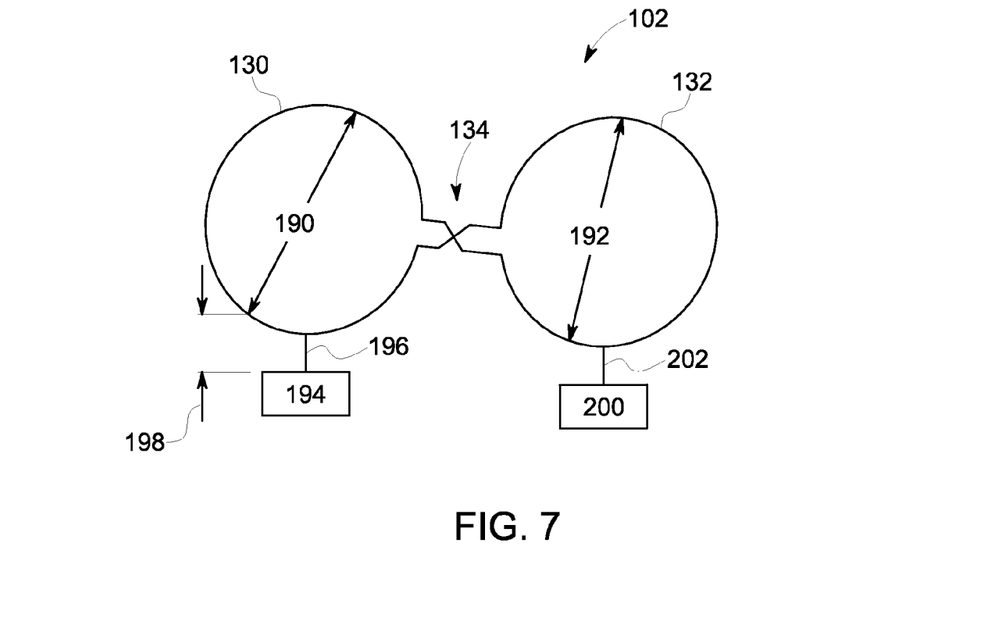
FIG. 7 is a perspective view of a second saddle coil shown in FIGS. 1-3 and formed in accordance with various embodiments.

FIG. 7 is a top view of the second saddle coil 102. As shown in FIG. 7, the third coil portion 130 is electrically connected to the fourth coil portion 132 via a coil connecting portion 134. The coil connecting portion 134 represents two electric paths crossing proximate to the location 150 that is selected to provide the optimal SNR, for imaging a selected region of interest. Thus, the third coil portion 130, the fourth coil portion 132 and the connecting portion 134 together form the closed-loop second saddle receive coil 102. In the exemplary embodiment, the location 150 (also shown in FIG. 3) is selected to improve the imaging of a subject's prostate gland. Accordingly, the location 150 where the saddle coil 100 and the saddle coil 102 cross paths is positioned externally on the subject at the location 150 that is nearest the prostate gland. Moreover, it should be realized that in the exemplary embodiment, the first saddle coil connecting portion 114 and the second saddle coil connecting portion 134 overlap at the location 150 and the first saddle coil connecting portion 114 is substantially parallel with the second saddle coil connecting portion 134 at the location 150.

In the exemplary embodiment, the second saddle coil 102 is also configured as a receive-only coil. Accordingly, the second saddle coil 102 has a shape that enables the third coil portion 130 to be inserted over one leg and the fourth coil portion 132 to be inserted over another leg. In the exemplary embodiment, the third coil portion 130 is substantially circular and has a diameter 190. Moreover, the fourth coil portion 132 is substantially circular and has a diameter 192 that is substantially the same as the diameter 190. Thus, an overall length of the third and fourth coil portions 130 and 132 is selected to enable the third and fourth coil portions 130 and 132 to be positioned at the upper end of the subject's legs where the subject's legs join the torso, as shown in FIGS. 4 and 5, for example.

As shown in FIG. 7, the coil apparatus 10 may also include a third electronics assembly 194 that is electrically connected to the third coil portion 130 via a cable 196. The electronics assembly 194 generally includes an RF receiver for receiving signals from the third coil portion 130. The electronics assembly 194 may also include capacitors, inductors, baluns, or other components to improve the SNR of the third coil portion 130. In the exemplary embodiment, the cable 196 is an RF cable having a predetermined length 198. For example, a balun device may be utilized to reduce the noise and/or stray RF currents generated due to induced currents in the RF cable 196, as discussed above.

Accordingly, the length 196 of the RF cable 196 is determined based on the wavelength of a signal transmitted through the RF cable 196. In the exemplary embodiment, the fourth coil portion 132 is formed substantially similar to the third coil portion 130. Additionally, the fourth coil portion 132 may be coupled to a second electronics assembly 200 via a second RF cable 202. Optionally, the third and fourth coil portions 130 and 132 may be coupled to a single electronics assembly, such as electronics assembly 170 or 194, for example. In the exemplary embodiment, the electronic assemblies 170, 180, 194, and 200 and the associated coil portions 110, 112, 130, and 132 form a quadrature receiving circuit. More specifically, magnetic resonance signals received by the saddle coils 100 and 102 are quadrature-received by the quadrature receiving assemblies 170, 180, 194, and 200 to facilitate improving the SNR of magnetic resonance signals received by the RF coil portions 110, 112, 130, and 132.

Figure 8:
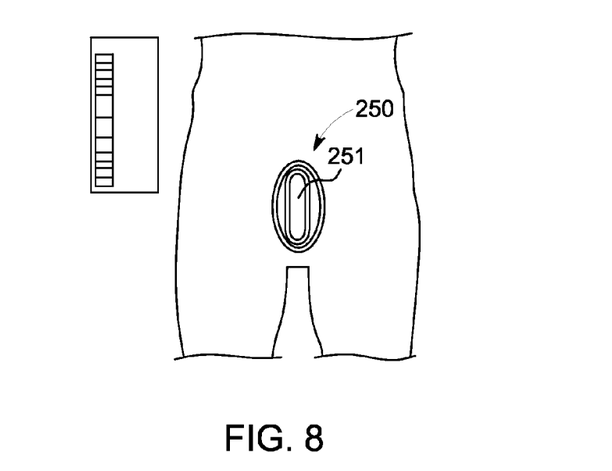
FIG. 8 is an exemplary coronal plane image generated using a conventional endorectal probe.
Figure 9:
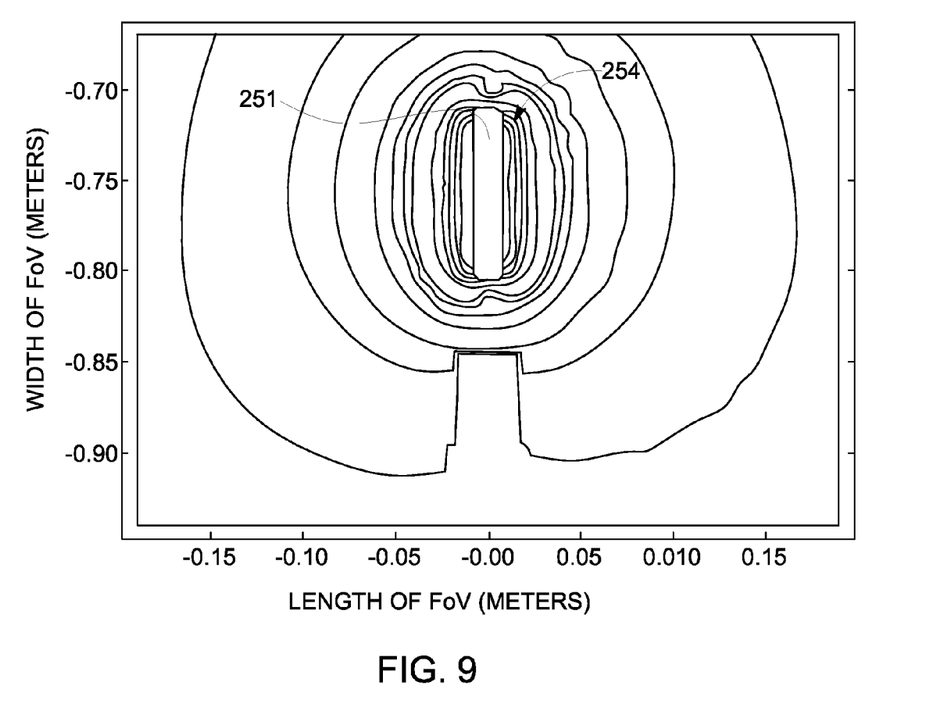
FIG. 9 is another exemplary coronal plane image generated using a conventional endorectal probe.
Figure 10:
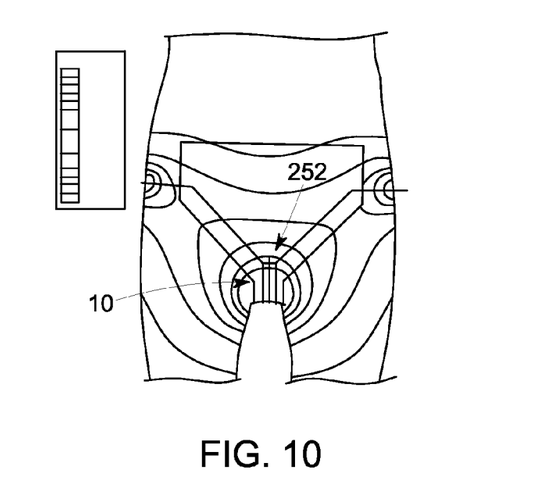
FIG. 10 is an exemplary coronal plane image that may be generated using the coil apparatus shown in FIGS. 1-7 in accordance with various embodiments.
Figure 11:
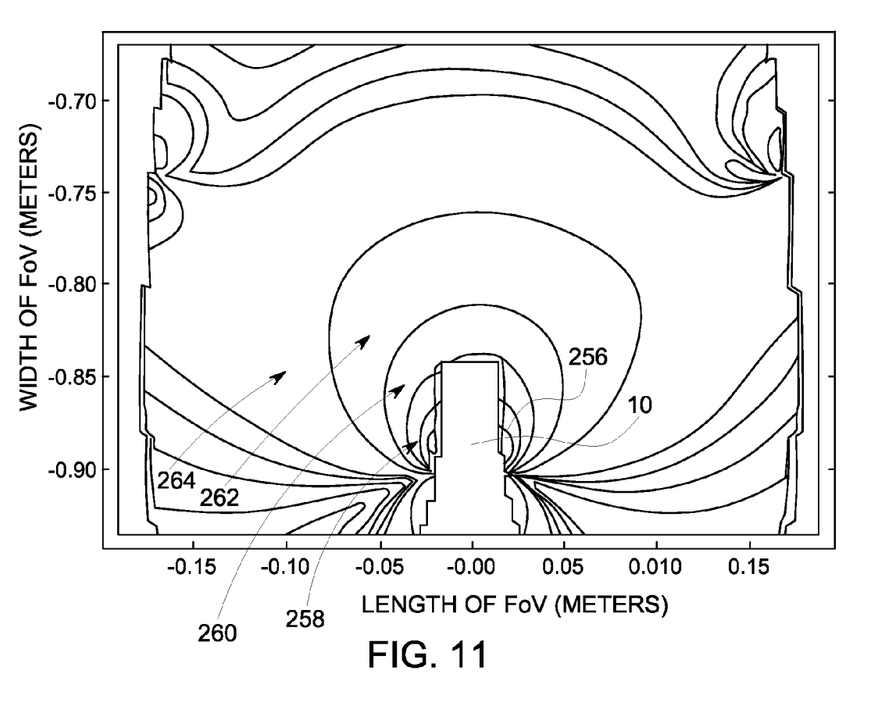
FIG. 11 is another exemplary coronal plane image that may be generated using the coil apparatus shown in FIGS. 1-7 in accordance with various embodiments.
Figure 12:
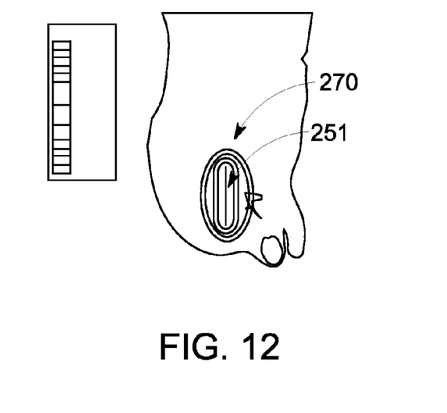
FIG. 12 is an exemplary sagittal plane image generated using a conventional endorectal probe.
Figure 13:
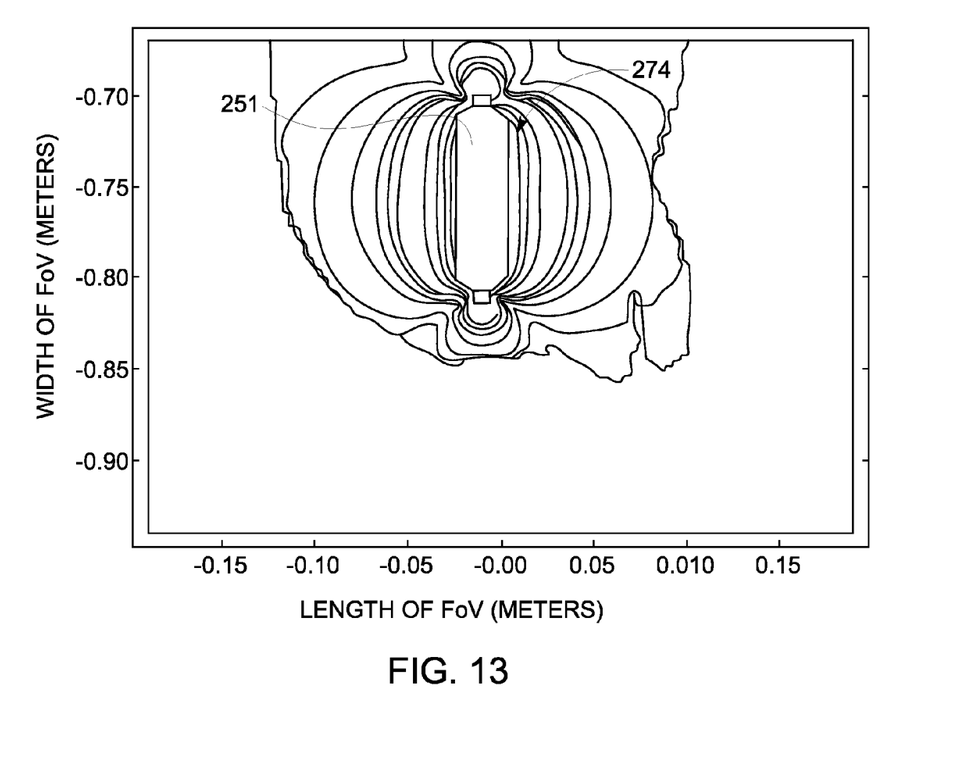
FIG. 13 is an exemplary sagittal plane image generated using a conventional endorectal probe.
Figure 14:
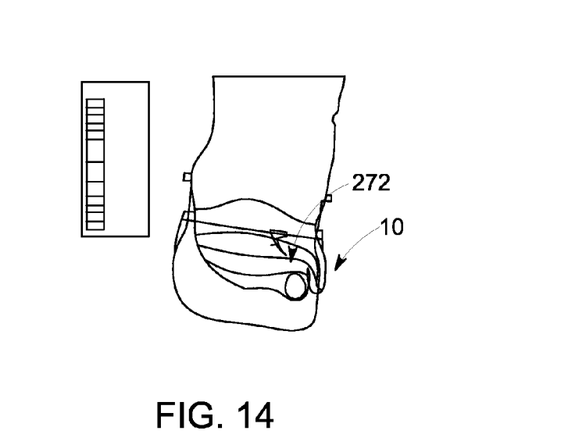
FIG. 14 is exemplary sagittal plane image that may be generated using the coil apparatus shown in FIGS. 1-7 in accordance with various embodiments.
Figure 15:
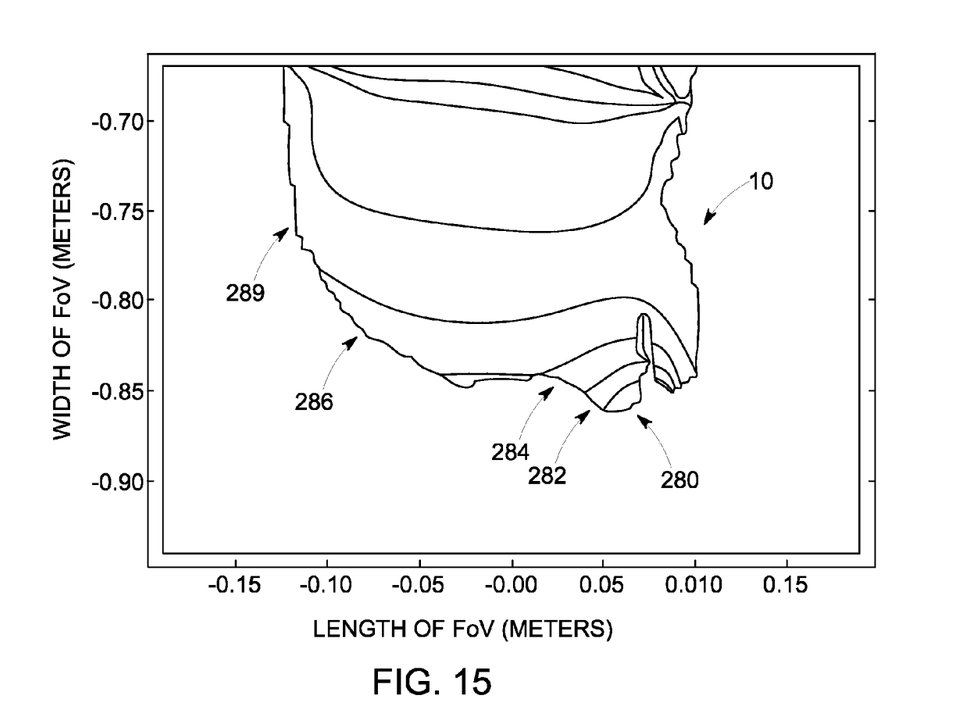
FIG. 15 is another exemplary sagittal plane image that may be generated using the coil apparatus shown in FIGS. 1-7 in accordance with various embodiments.

For example, FIG. 8 is an exemplary coronal plane image that illustrates the magnetic field sensitivity of a conventional endorectal probe. FIG. 9 is an exemplary coronal plane image that illustrates the SNR of the conventional endorectal probe. FIG. 10 is an exemplary coronal plane image that illustrates the magnetic field sensitivity of the coil apparatus 10. FIG. 11 is an exemplary coronal plane image that illustrates the SNR of the coil apparatus 10. FIG. 12 is an exemplary sagittal plane image that illustrates the magnetic field sensitivity of the conventional endorectal probe. FIG. 13 is an exemplary sagittal plane image that illustrates the SNR of the conventional endorectal probe. FIG. 14 is an exemplary sagittal plane image that illustrates the magnetic field sensitivity of the coil apparatus 10. FIG. 15 is an exemplary sagittal plane image that illustrates the SNR of the coil apparatus 10.

Referring to FIG. 8, the lightly shaded region 250 indicates the magnetic field reception strength of a conventional endorectal probe 251. The shaded region 252 in FIG. 10 illustrates the magnetic field reception strength of the coil apparatus 10. As shown in FIGS. 8 and 10, it is clear that the magnetic field sensitivity of the coil apparatus 10 is greater than the magnetic field sensitivity of the conventional endorectal probe 251.

As discussed above, FIGS. 9 and 11 illustrate the SNR of the conventional endorectal probe 251 and the SNR of the coil apparatus 10, respectively. Specifically, the X-axis represents a width of the FOV of the conventional endorectal probe 251 and a width of the FOV of the coil apparatus 10 in meters and the Y-axis represents a height of the FOV of the conventional endorectal probe 251 and a height of the FOV of the coil apparatus 10 in meters. As shown in FIG. 9, the SNR in an area 254 proximate to the conventional endorectal probe 251 is relatively strong. However, the contour plot in FIG. 9 also indicates that the SNR rapidly decreases a short distance from the conventional endorectal probe 251. In contrast, the contour plot of the coil apparatus 10 shown in FIG. 11 illustrates that the SNR is relative high in an area 256 nearest the coil apparatus 10. Moreover, rather than the SNR rapidly declining outside the area 256, the SNR of the coil apparatus 10 gradually declines as shown in areas 258, 260, 262, and 264. Thus, the coil apparatus 10 has an improved SNR over larger distances in the FOV.

Similarly, and referring to FIG. 12, a lightly shaded region 270 indicates the magnetic field reception strength of the conventional endorectal probe 251. The shaded region 272 in FIG. 14 illustrates the magnetic field reception strength of the coil apparatus 10.

Additionally, as discussed above, FIGS. 13 and 15 are sagittal plane images that illustrate the SNR of the conventional endorectal probe 251 and the SNR of the coil apparatus 10, respectively. Specifically, the X-axis represents a width of the FOV of the conventional endorectal probe 251 and a width of the FOV of the coil apparatus 10 in meters and the Y-axis represents a height of the FOV of the conventional endorectal probe 251 and a height of the FOV of the coil apparatus 10 in meters. As shown in FIG. 13, the SNR in an area 274 proximate to the conventional endorectal probe 152 is relatively strong. However, the contour plot in FIG. 13 also indicates that the SNR rapidly decreases a short distance from the conventional endorectal probe 251. In contrast, the contour plot of the coil apparatus 10 shown in FIG. 5 illustrates that the SNR is high in an area 280 nearest the coil apparatus 10. Moreover, rather than the SNR rapidly declining outside the area 280, the SNR of the coil apparatus 10 gradually declines as shown in areas 282, 284, 286, and 288. Thus, the coil apparatus 10 has an improved SNR over larger distances in the FOV than the conventional endorectal probe 251.

Figure 16:
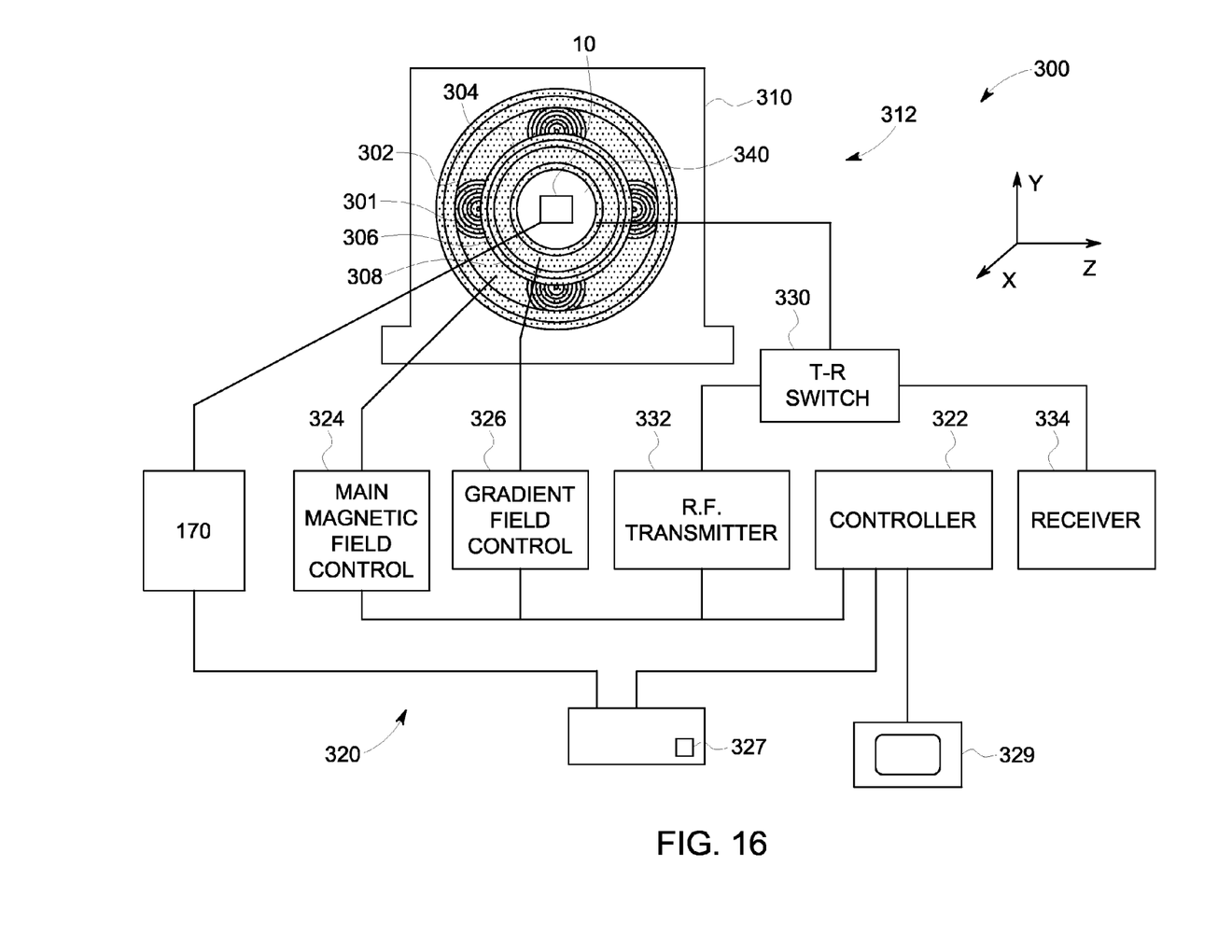
FIG. 16 is a schematic block diagram of a Magnetic Resonance Imaging (MRI) system formed in accordance with various embodiments.

FIG. 16 is a schematic illustration of an exemplary MRI imaging system 300 that may be utilized with the coil apparatus 10, shown in FIGS. 1-7. In the exemplary embodiment, the imaging system 300 includes a superconducting magnet 301 formed from magnetic coils supported on a magnet coil support structure. However, in other embodiments, different types of magnets may be used, such as permanent magnets or electromagnets. A vessel 302 (also referred to as a cryostat) surrounds the superconducting magnet 301 and is filled with liquid helium to cool the coils of the superconducting magnet 301. A thermal insulation 304 is provided surrounding the outer surface of the vessel 302 and the inner surface of the superconducting magnet 301. A plurality of magnetic gradient coils 306 are provided within the superconducting magnet 301 and an RF transmit coil 308 is provided within the plurality of magnetic gradient coils 306.

The imaging system 300 also includes the MRI coil apparatus 10 which in operation is worn by a subject and disposed within a bore 340 of the imaging system 300 when the subject is moved within the bore 340. The components described above are positioned within a gantry 310 and generally form an imaging portion 312. It should be noted that although the superconducting magnet 301 is a cylindrical shaped, other shapes of magnets can be used.

A processing portion 320 generally includes a controller, such a electronics assembly 170 for operating the coil apparatus 10, a controller 322, a main magnetic field control 324, a gradient field control 326, a computer 327, a display device 328, a transmit-receive (T-R) switch 330, an RF transmitter 332 and a receiver 334. In the exemplary embodiment, the computer 327 is programmed to receive information from the coil apparatus 10. Based on the received information, the computer 327 generates an image of the subject.

In operation, the subject, after being positioned in the coil apparatus 10 (shown in FIG. 1), is inserted into a bore 340 of the imaging system 300. The superconducting magnet 301 produces an approximately uniform and static main magnetic field $B_0$ across the bore 340. The strength of the electromagnetic field in the bore 340 and correspondingly in the subject, is controlled by the controller 322 via the main magnetic field control 324, which also controls a supply of energizing current to the superconducting magnet 301. Moreover, RF information is transmitted from the coil apparatus 10 to the computer 327, via the electronics assembly 170.

The magnetic gradient coils 306, which include one or more gradient coil elements, are provided so that a magnetic gradient can be imposed on the magnetic field $B_0$ in the bore 340 within the superconducting magnet 301 in any one or more of three orthogonal directions x, y, and z. The magnetic gradient coils 306 are energized by the gradient field control 326 and are also controlled by the controller 322.

The RF transmit coil 308 is arranged to transmit magnetic pulses and/or optionally simultaneously detect MR signals from the subject. The RF transmit coil 308 is selectably interconnected to one of the RF transmitter 332 or the receiver 334, respectively, by the T-R switch 330. The RF transmitter 332 and T-R switch 330 are controlled by the controller 322 such that RF field pulses or signals are generated by the RF transmitter 332 and selectively applied to the subject for excitation of magnetic resonance in the subject.

Following application of the RF pulses, the T-R switch 330 is again actuated to decouple the RF transmit coil 308 from the RF transmitter 332. The MR signals detected by the coil apparatus 10 are in turn communicated to the computer 327, via the electronics assembly 170. The detected signals are then utilized to generate an image of the subject. Specifically, the detected signals are utilized to generate in improved image of the pelvic region of a subject to enable a physician to more clearly view the prostate gland.

A technical effect of some of the various embodiments described herein is to improve MR image quality. In one embodiment, the lotus-shaped surface coil includes a pair of saddle coils that are arranged to follow the contour of the subject's legs to provide a large FOV of the pelvic region while concurrently providing an increased SNR.

Various embodiments described herein provide a tangible and non-transitory machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be electrically connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A Radio Frequency (RF) coil apparatus for Magnetic Resonance (MR) imaging, said coil apparatus comprising:
   a body adapted to be worn by a subject being scanned, the body comprising an anterior portion, a posterior portion, and a transition portion coupled between the anterior and posterior portions;
   a first RF receive-only saddle coil including a first coil positioned in the anterior portion and a second coil positioned in the anterior portion, the first RF saddle coil configured to be positioned on the anterior and posterior sides of the subject; and
   a second RF receive-only saddle coil including a third coil configured to receive a first leg of the subject therein and a fourth coil configured to receive a second leg of the subject therein, a portion of the third and fourth coils being positioned in both the anterior portion and the posterior portion.

2. The RF coil of claim 1, wherein the first and second coils have a substantially trapezoidal shape.

3. The RF coil of claim 1, wherein the first coil comprises a pair of coil portions that taper inwardly from an upper edge of the anterior portion to the transition portion, and the second coil comprises a second pair of coil portions that taper inwardly from an upper edge of the posterior portion to the transition portion.

4. The RF coil of claim 1, wherein the transition portion comprises an opening extending therethrough, the opening sized to receive a medical device therethrough.

5. The RF coil of claim 1, wherein the first and second saddle coils are arranged within the body to form a quadrature RF signal receiving circuit.

6. The RF coil of claim 1, wherein the first saddle coil is offset from the second saddle coil by approximately 90 degrees.

7. The RF coil of claim 1, wherein the first saddle coil has a trapezoidal shape configured to conform to the subject's pelvis.

8. The RF coil of claim 1, wherein the first saddle coil overlaps the second saddle coil at a predetermined location that is nearest to a subject's prostate gland.

9. The RF coil of claim 1, wherein the body comprises only the first and second saddle coils, the first and second saddle coils being configured to couple to an external electronics assembly.

10. A Magnetic Resonance Imaging (MRI) system comprising:
    a main magnet configured to generate a main magnetic field within a bore of the imaging system; and
    a Radio Frequency (RF) coil apparatus configured to be worn by a subject being inserted into the bore of the imaging system, the coil apparatus comprising a body adapted to be worn by a subject being scanned, the body comprising an anterior portion, a posterior portion, and a transition portion coupled between the anterior and posterior portions;

a first RF receive-only saddle coil including a first coil positioned in the anterior portion and a second coil positioned in the anterior portion, the first RF saddle coil configured to be positioned on the anterior and posterior sides of the subject; and a second RF receive-only saddle coil including a third coil configured to receive a first leg of the subject therein and a fourth coil configured to receive a second leg of the subject therein, a portion of the third and fourth coils being positioned in both the anterior portion and the posterior portion.

11. The MRI system of claim 10, wherein the first and second coils have a substantially trapezoidal shape.

12. The MRI system of claim 10, wherein the first coil comprises a pair of coil portions that taper inwardly from an upper edge of the anterior portion to the transition portion, and the second coil comprises a second pair of coil portions that taper inwardly from an upper edge of the posterior portion to the transition portion.

13. The MRI system of claim 10, wherein the transition portion comprises an opening extending therethrough, the opening sized to receive a medical device therethrough.

14. The MRI system of claim 10, wherein the first and second saddle coils are arranged within the body to form a quadrature RF signal receiving circuit.

15. The MRI system of claim 10, wherein the first saddle coil is offset from the second saddle coil by approximately 90 degrees.

16. The MRI system of claim 10, wherein the first saddle coil has a trapezoidal shape configured to conform to the subject's pelvis.

17. The MRI system of claim 10, wherein the first saddle coil overlaps the second saddle coil at a predetermined location that is nearest to a subject's prostate gland.

18. The MRI system of claim 10, wherein the body comprises only the first and second saddle coils, the first and second saddle coils being configured to couple to an external electronics assembly.

19. A method of imaging a subject using a Magnetic Resonance Imaging (MRI) system, said method comprising:

positioning a subject within an RF coil apparatus such that a first RF receive-only coil is positioned in the anterior portion of the subject, a second RF receive-only coil is positioned on an anterior portion of the subject, a third RF coil is positioned around a first leg of the subject, and a fourth RF receive-only coil is positioned around a second leg of the subject; and generating an image of the subject using information received from the first, second, third and fourth RF receive-only coils.

20. The method of claim 19, wherein the first and second receive-only RF coils have a trapezoidal shape.

* * * * *

UNITED STATES PATENT AND TRADEMARK OFFICE
CERTIFICATE OF CORRECTION

PATENT NO. : 8,598,880 B2
APPLICATION NO. : 13/110611
DATED : December 3, 2013
INVENTOR(S) : Taylan Dalveren, Victor Taracila and David Berendt It is certified that error appears in the above-identified patent and that said Letters Patent is hereby corrected as shown below:

In the Specification

In Brief Description of the Invention,

Column 1, line 51, delete "anterior", and insert therefor -- posterior --.

Column 2, line 2, delete "anterior", and insert therefor -- posterior --.

Column 2, line 16, delete "anterior", and insert therefor -- posterior --.

In the Claims

Claim 1, column 10, line 25, delete "anterior", and insert therefor -- posterior --.

Claim 10, column 11, line 7, delete "anterior", and insert therefor -- posterior --.

Claim 19, column 12, line 19, delete "anterior", and insert therefor -- posterior --.

Signed and Sealed this
Third Day of March, 2015

Michelle K. Lee
*Deputy Director of the United States Patent and Trademark Office*